United States Patent [19]

Chittenden

[11] 4,160,451
[45] Jul. 10, 1979

[54] UNIDIRECTIONAL CATHETER PLACEMENT UNIT

[75] Inventor: Richard M. Chittenden, Grayslake, Ill.

[73] Assignee: Abbott Laboratories, North Chicago, Ill.

[21] Appl. No.: 854,858

[22] Filed: Nov. 25, 1977

[51] Int. Cl.² .............................................. A61M 5/00
[52] U.S. Cl. .................................. 128/214.4; 226/188; 254/175.5
[58] Field of Search ..................... 128/214.4, 349, 350, 128/276, DIG. 16; 226/188; 242/219, 217, 72; 254/175.5, 175.3, 150 R; 192/41 R, 41 S, 45, 46

[56] References Cited

U.S. PATENT DOCUMENTS

| 3,561,445 | 2/1971 | Katerndahl | 128/214.4 |
| 3,838,688 | 10/1974 | May et al. | 128/214.4 |
| 3,995,628 | 12/1976 | Gula et al. | 128/214.4 |

Primary Examiner—E. H. Eickholt
Attorney, Agent, or Firm—Aaron L. Hardt; Robert L. Niblack

[57] ABSTRACT

A unidirectional, needle outside, reel-type catheter placement unit is disclosed. The unidirectional unit obviates severing of the catheter by the needle, which can occur when the catheter is retracted in bidirectional units. Preferably, the catheter placement unit comprises an overcap or cover which is only coupled to the reel of the reel-type catheter placement unit by a ball clutch when the overcap is rotated in a direction that advances the catheter from the unit.

10 Claims, 5 Drawing Figures

UNIDIRECTIONAL CATHETER PLACEMENT UNIT

BACKGROUND OF THE INVENTION

The present invention relates to catheter placement units and, more particularly, to catheter placement units of the reel type disclosed in U.S. Pat. No. 3,561,445 granted Feb. 9, 1971 to D. Katerndahl, et al. and U.S. Pat. No. 3,995,628 granted Dec. 7, 1976 to J. Gula, et al.

Both the Katerndahl, et al. and Gula, et al. units are bidirectional. That is, the catheters wound therein can be both advanced from and retracted into the container of the unit. On occasion, while the needle is inserted into the vein of a patient, the nurse or doctor inserting the catheter might inadvertently rotate the reel in a manner that retracts the catheter into the container and severs it on the heel of the needle of the unit. When the catheter is again advanced from the unit into the patient, the severed portion of the catheter is freely disposed in the patient's vein. Then, when the catheter is subsequently removed from the patient's vein, the freely disposed, severed portion of the catheter will remain in the patient's vein. In most instances, surgery is then required to remove the severed portion of the catheter from the patient, once it is recognized that the severed portion is still in the patient.

While stringent precautions can be taken to avoid such severing of the catheter and to assure that the entire catheter is removed from the patient when infusions therethrough are completed, it will be apparent that a catheter placement unit which prevents retraction of the catheter into the container of the unit will substantially obviate the problem.

SUMMARY OF THE INVENTION

Therefore, it is the primary object of this invention to provide a unidirectional, needle outside, reel-type catheter placement unit from which the catheter can be advanced, but not retracted. Another object is to provide such a catheter placement unit wherein the catheter may be wound into the container during manufacture of the unit, but not thereafter. Still another object of the present invention is to provide such a catheter placement unit wherein the means for preventing the unwanted retraction from occuring is hidden from the sight and touch of the user thereof to substantially prevent that means from being intentionally overridden.

In accordance with these and other objects, there is provided by the present invention a catheter placement unit comprising an enclosed container having a base portion including an outlet from the container and an upper portion including a reel for a catheter. The upper portion is rotatably mounted on the base portion of the container. A hollow needle having a pointed distal end is secured at its proximal end to the base portion of the container in communication with the outlet therefrom. A catheter is wound on the reel of the upper portion of the container and extends through the outlet into the hollow needle so that rotating the upper portion relative to the base portion advances or retracts the catheter into or out of the container through the needle. A clutch in cooperation with the upper portion of the container allows the upper portion to be manually rotated only in the direction that advances the catheter when the unit is fully assembled. Preferably, the clutch includes a rotatably mounted cover or overcap overlying the upper portion of the container and concealing the means for coupling the cover to the upper portion. Preferably, a ball bearing mechanism can be used for coupling the cover to the upper portion.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

The teachings of U.S. Pat. No. 3,561,445 described hereinabove are incorporated herein by this reference thereto.

Figure 1:
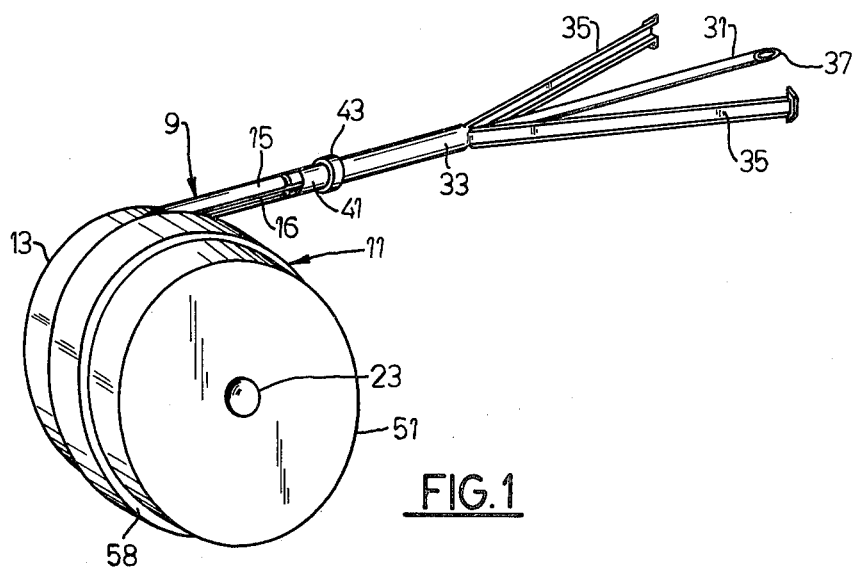
FIG. 1 is a perspective view of a preferred embodiment of the unidirectional, needle outside, reel-type catheter placement unit of the present invention.
Figure 2:
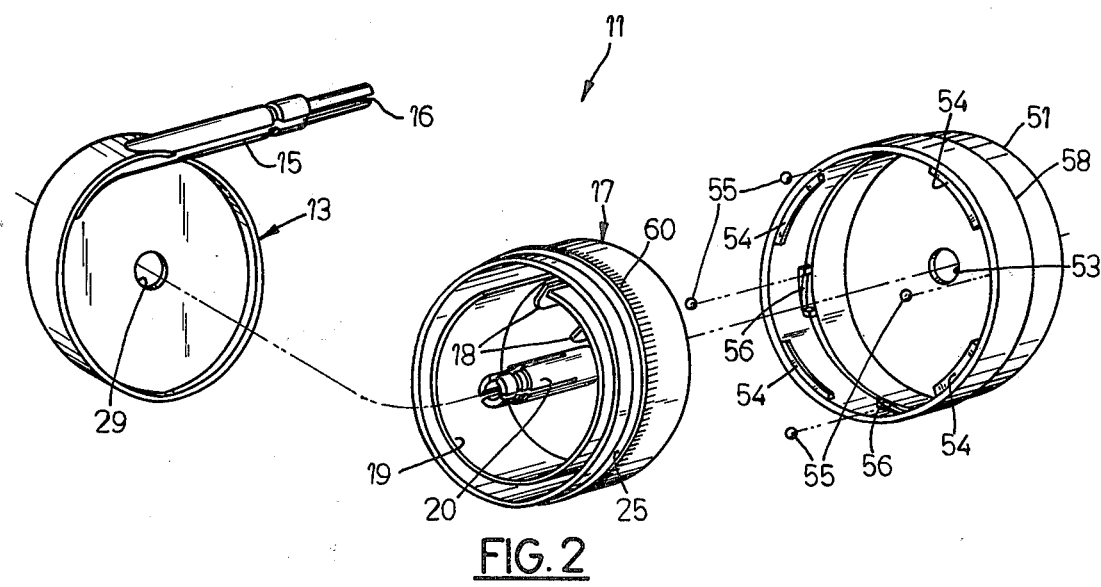
FIG. 2 is an exploded view of the container and overcap of the device of FIG. 1.
Figure 4:
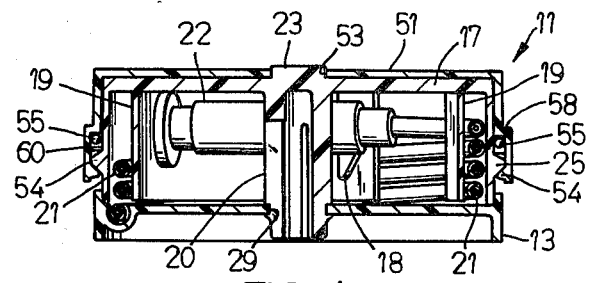
FIG. 4 is a cross-sectional view along the line 4—4 in FIG. 3 of the device thereof.

Referring to the drawing, there is shown in FIG. 1 a preferred embodiment of a unidirectional, needle outside, reel-type catheter placement unit shown generally as 9. Catheter placement unit 9 comprises an enclosed container shown generally as 11 in FIG. 1. Container 11 has a cylindrical base portion 13 including a tangentially extending outlet 15 therefrom which has a longitudinal slit 16 therealong. Container 11 has a cylindrical upper portion 17 including lugs 18 and a reel 19 on which a catheter 21 having a catheter hub 22 at its proximal end can be wound. Upper portion 17 is rotatably mounted on base portion 13 by means of spindle 20 integral to upper portion 17, which spindle is inserted into an aperture 29 of base portion 13. As can be seen in FIG. 4, the upper end 23 of spindle 20 extends outwardly from upper portion 17 of container 11. Upper portion 17 has an integral annular rim 25 on its outer circumferential surface.

A hollow needle 31 covered by a hollow sheath 33 having separable wing portions 25 has a pointed distal end 37 and a proximal end 41 secured to container 11 in communication with outlet 15. Hollow needle 31, preferably, has its proximal end 41 embedded within sheath 33. Collar 43 is slidable on sheath 33 to allow wings 35 to be opened when it is at the proximal end of sheath 33 and closed when it is at the distal end.

Figure 3:
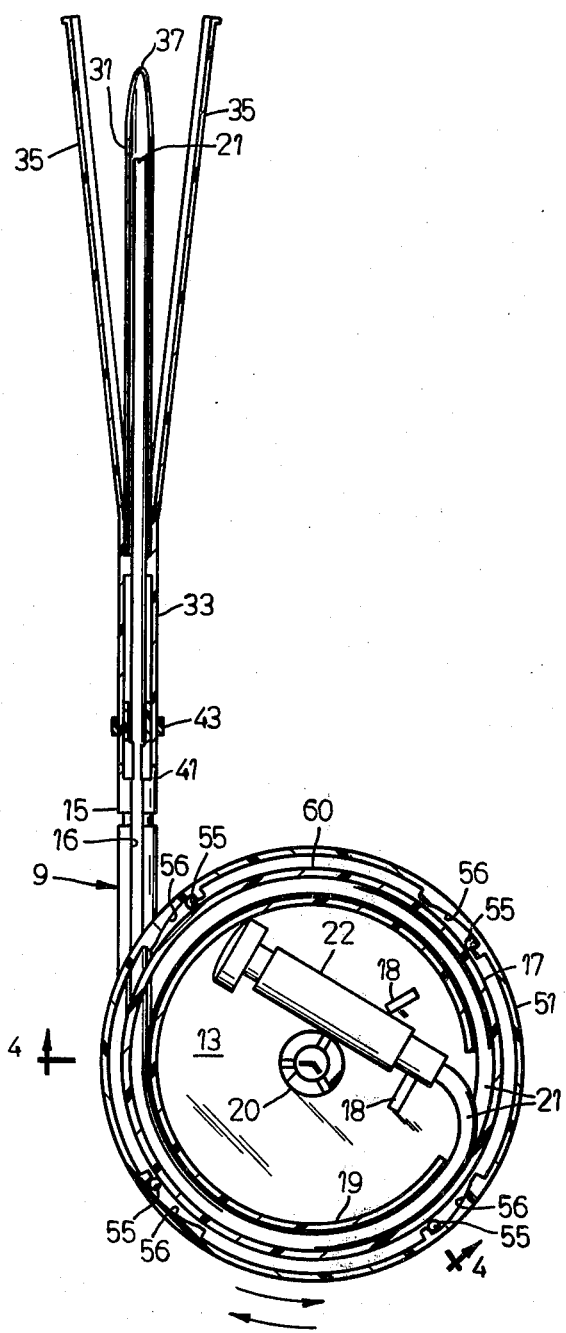
FIG. 3 is a top view of the device of FIG. 1 wherein the container and overcap portions are shown in cross-section and the needle portion is shown in a partial cross-section.
Figure 5:
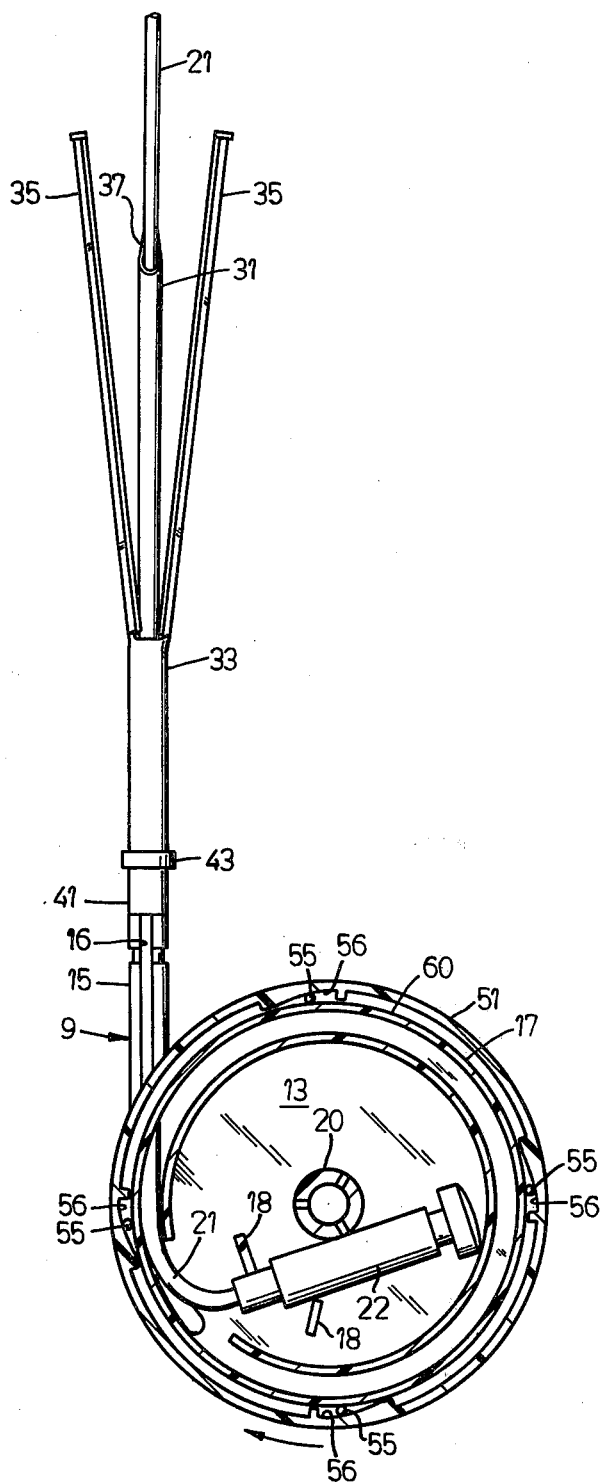
FIG. 5 is a top view of the device of FIG. 1 showing the container and overcap portions in cross-section and the catheter unwound from the reel and extending out of the needle thereof.

Catheter 21 is wound on reel 19 of container 11 and extends through outlet 15 into hollow needle 31 so that rotating upper portion 17 clockwise relative to base portion 13 causes catheter 21 to advance through outlet 15 and out of needle 31 at its pointed distal end 37. Likewise, rotating upper portion 17 counterclockwise relative to base portion 13 causes catheter 21 to be retracted into container 11 through hollow needle 31 and outlet 15. Advantageously, catheter 21 can be wound onto reel 19 during the manufacture of catheter placement unit 9 by forcing a portion of catheter 21 through the longitudinal slot 16 of outlet 15 and locating catheter hub 22 on base portion 13 so that it lies between hubs 18 and spindle 20 of upper portion 17 when spindle 20 is inserted into aperture 29 of base portion 13, as illustrated in FIG. 3. By rotating upper portion 17 counterclockwise to base portion 13, the entire length of catheter 21 can then be wound onto reel 19.

An overcap or cover 51 is rotatably mounted over upper portion 17 of container 11 by insertion of the outer end 23 of spindle 20 through aperture 53 of cover 51. Cover 51 also has a plurality of flanges 54 extending inwardly from the circumference thereof at its bottom. Flanges 54 engage annular rim 25 of upper portion 17 to more firmly secure cover 51 to upper portion 17. In the preferred embodiment of the catheter placement unit 9 of the present invention, cover 51 conceals upper portion 17 from sight and touch.

Cover 51 has a plurality of balls 55 captured in a plurality of raceways 56 disposed on its inner surface. Each raceway 56 has a pair of endwalls extending substantially radially from the circumference of cover 51, one sidewall along the circumference of cover 51 and an upperwall formed by annular shoulder 58 of cover 51. Each raceway 56 has a width at one endwall thereof at least substantially equal to the diameter of its captured ball 55. The width of raceway 56 continuously decreases to the other endwall of raceway 56. Preferably, raceway 56 has an arcuate sidewall eccentric to the inner circumferential surface of cover 51.

When cover 51 overlies upper portion 17, a ball 55 is disposed in each raceway 56 and annular rim 25 of upper portion 17 provides a continuous lower surface for the plurality of raceways 56, while the outer circumferential surface 60 just above annular rim 25 provides a second sidewall for each raceway 56. Preferably, the surface 60 serving as a second sidewall for raceway 56 can be roughened, grooved, or otherwise treated to increase its frictional characteristics.

When cover 51 is rotated clockwise relative to base portion 13, balls 55 with be contacted by the narrow ends of raceways 56 and wedged against the outer surface 60 of upper portion 17. When the plurality of balls 55 are wedged against upper portion 17, upper portion 17 rotates in a clockwise direction with cover 51 to advance catheter 21 from container 11 through outlet 15 and needle 31.

However, when cover 51 is rotated in a counterclockwise direction relative to base portion 13, the plurality of balls 55 ride on the annular rim 25 of upper portion 17 at the widest end of raceways 56 without engaging upper portion 17, while the radially extending endwalls of raceways 56 at their widest ends push balls 55 along the rim 25. Thus, cover 51 is not coupled to upper portion 17 when the cover is rotated in a counterclockwise direction to base portion 13 and, therefore, catheter 21 cannot be retracted into container 11 by means of cover 51. Accordingly, it will be clear that overcap or cover 51 in combination with balls 55 and raceways 56 provides a clutch which cooperates with upper portion 17 to allow the upper portion to be manually rotated only in the direction that advances catheter 21 out of needle 31 at its distal point 37.

It will be apparent to those skilled in the art, that the raceways 56 can be otherwise designed and/or situated without changing their purpose or functionality. For example, shoulder 58 can be eliminated from cover 51, if it is replaced by a second annular rib on upper portion 17 located above rim 25 a distance substantially equal to the diameter of balls 55. Further, it will be apparent that raceways 56 and annular rim 25 can be interchanged on upper portion 17 and cover 51.

Likewise, it will also be apparent that numerous clutch means, such as a ratchet, can be used in place of the preferred ball clutch described herein to couple cover 51 to upper portion 17. Accordingly, as I have now described the invention in specific detail and exemplified the manner in which it may be carried into practice, it will be readily apparent to those skilled in the art that innumerable variations, applications, modifications and extensions of the basic principles involved may be made without departing from its sphere or scope.

That which I claim is:

1. In a catheter placement unit comprising:
   an enclosed container having a base portion including an outlet from said container and an upper portion including a reel for a catheter, said upper portion rotatably mounted on said base portion;
   a hollow needle having a pointed distal end and a proximal end secured to said container in communication with said outlet therefrom; and
   a catheter wound on said reel of said container and extending through said outlet into said hollow needle so that rotating said upper portion relative to said base portion advances or retracts said catheter out of or into said needle; the improvement which comprises the addition to said catheter placement unit of:
   a clutch cooperable with said upper portion to allow said upper portion to be manually rotated only in the direction that advances said catheter,
   said clutch including a rotatably mounted cover overlying and concealing said upper portion and means for coupling said cover to said upper portion only when said cover is rotated in the direction predetermined to rotate said upper portion in the direction that advances said catheter.

2. The catheter placement unit defined in claim 1 wherein said means for coupling said cover to said upper portion includes a ball confined between an outer surface of said upper portion and an inner surface of said cover in a raceway having a width at one endwall thereof at least substantially equal to the diameter of said ball and continuously decreasing to the other endwall of said raceway.

3. The catheter placement unit defined in claim 2 wherein said raceway is integral to an inner surface of said cover.

4. The catheter placement unit defined in claim 3 wherein said raceway has an arcuate sidewall eccentric to said inner surface of said cover.

5. The catheter placement unit defined in claim 3 wherein said raceway is located in the inner surface of said cover.

6. The catheter placement unit defined in claim 3 wherein said upper portion has an annular rim on its outer cylindrical surface to further confine said ball between said upper portion and said cover.

7. The catheter placement unit defined in claim 2 wherein said clutch includes a plurality of said balls confined in a plurality of said raceways.

8. In a catheter placement unit comprising:
   an enclosed substantially cylindrical container having a cylindrical base portion enclosed at its bottom with an outlet extending tangentially therefrom and a cylindrical upper portion enclosed at its top with a reel therein for a catheter, said upper portion rotatably mounted on said base portion;

a hollow needle having a pointed distal end and a proximal end secured to said container in communication with said outlet therefrom; and a catheter wound on said reel of said container and extending through said outlet into said hollow needle so that rotating said upper portion relative to said base portion advances or retracts said catheter into or out of said needle; the improvement which comprises the addition to said catheter placement unit of:

a clutch cooperable with said upper portion to allow said upper portion to be manually rotated only in the direction that advances said catheter, said clutch including a rotatably mounted cylindrical cover enclosed at its top, overlying and concealing said upper portion, and a plurality of balls confined between the outer cylindrical surface of said upper portion and the inner cylindrical surface of said cover in a plurality of raceways formed on the inner cylindrical surface of said cover, each of said raceways having a width at one endwall thereof at least substantially equal to the diameter of the ball confined therein and continuously decreasing along an arc eccentric to said inner surface of said cover to the other endwall of said raceway.

9. The catheter placement unit defined in claim 8 wherein said upper portion has an annular rim on its outer cylindrical surface to further confine said balls between said upper portion and said cover.

10. The catheter placement unit defined in claim 9 wherein said upper portion has an annular roughened area above said annular rim adapted to increase the friction between said balls and said upper portion.

* * * * *